United States Patent
Euvrard

(10) Patent No.: US 7,207,798 B2
(45) Date of Patent: Apr. 24, 2007

(54) MECHANIZED DENTAL INSTRUMENT

(75) Inventor: Hubert Euvrard, Besancon (FR)

(73) Assignee: Micro-Mega International Manufactures, Besancon (FR)

( * ) Notice: Subject to any disclaimer, the term of this patent is extended or adjusted under 35 U.S.C. 154(b) by 0 days.

(21) Appl. No.: 10/549,160

(22) PCT Filed: May 28, 2004

(86) PCT No.: PCT/FR2004/001323

§ 371 (c)(1),
(2), (4) Date: Sep. 14, 2005

(87) PCT Pub. No.: WO2005/004741

PCT Pub. Date: Jan. 20, 2005

(65) Prior Publication Data

US 2006/0172256 A1    Aug. 3, 2006

(30) Foreign Application Priority Data

Jun. 12, 2003  (FR) .................................. 03 07090

(51) Int. Cl.
A61C 3/02 (2006.01)
(52) U.S. Cl. ...................................... 433/165; 408/226
(58) Field of Classification Search ................ 433/126, 433/237, 134, 165, 166; 408/241 B, 226
See application file for complete search history.

(56) References Cited

U.S. PATENT DOCUMENTS

| 1,688,136 | A |   | 10/1928 | Chayes et al. |
| 1,875,559 | A |   | 9/1932  | Brumm |
| 2,005,849 | A |   | 7/1935  | Skinner |
| 2,231,969 | A | * | 2/1941  | Tifft .............................. 433/126 |
| 2,344,605 | A |   | 3/1944  | Droegkamp |
| 2,568,315 | A |   | 9/1951  | Björklund |
| 2,785,464 | A | * | 3/1957  | Hoffmeister ................ 433/126 |
| 2,813,337 | A |   | 11/1957 | Uhler |
| 3,163,934 | A |   | 1/1965  | Wiseman |
| 3,368,279 | A |   | 2/1968  | Weissman |
| 3,472,045 | A |   | 10/1969 | Nelsen et al. |
| 3,751,176 | A |   | 8/1973  | Von Hollen |
| 4,014,099 | A |   | 3/1977  | Bailey |

(Continued)

FOREIGN PATENT DOCUMENTS

| FR | 2692473 | 12/1993 |
| GB | 587856  | 5/1947  |

Primary Examiner—Ralph A. Lewis
(74) Attorney, Agent, or Firm—Gary M. Cohen

(57) ABSTRACT

A mechanized dental instrument includes an active part (2) and a sleeve (3) arranged on an end of the dental instrument which opposes the active part. The sleeve (3) is provided with a rotary drive means (4) that can, when assembled with the head of a handpiece, directly engage with a rotary drive means located upstream of the head of the handpiece. The drive means (4) is produced from a flat metallic piece which is fixed to the active part (2) by being slid over the axle (2a) of the active part (2), and which is provided with at least one opening (5) that is shaped to enable the circulation of plastic material forming the sleeve (3) when the sleeve (3) is molded over the axle (2a) to ensure the connection of the rotary drive means (4) on the axle (2a).

10 Claims, 2 Drawing Sheets

U.S. PATENT DOCUMENTS

| | | | |
|---|---|---|---|
| 4,021,917 A * | 5/1977 | Nakanishi | 433/126 |
| 4,021,920 A | 5/1977 | Kirschner et al. | |
| 4,117,597 A * | 10/1978 | Trist et al. | 433/126 |
| 4,285,671 A | 8/1981 | Lustig et al. | |
| 4,449,932 A | 5/1984 | Lustig | |
| 4,451,237 A | 5/1984 | Filhol | |
| 4,478,578 A | 10/1984 | Leonard | |
| 4,486,175 A | 12/1984 | Fisher et al. | |
| 4,564,354 A | 1/1986 | Rosenstatter | |
| 4,941,828 A * | 7/1990 | Kimura | 433/114 |
| 5,007,832 A | 4/1991 | Meller et al. | |
| 5,040,978 A | 8/1991 | Falcon et al. | |
| 5,120,220 A | 6/1992 | Butler | |
| 5,252,067 A * | 10/1993 | Kakimoto | 433/129 |
| 5,730,595 A | 3/1998 | Bailey | |
| 5,897,318 A * | 4/1999 | Badoz | 433/165 |
| 5,941,705 A | 8/1999 | De Jackmo et al. | |
| 6,155,827 A * | 12/2000 | Euvrard | 433/133 |
| 6,579,093 B2 * | 6/2003 | Bailey et al. | 433/132 |

* cited by examiner

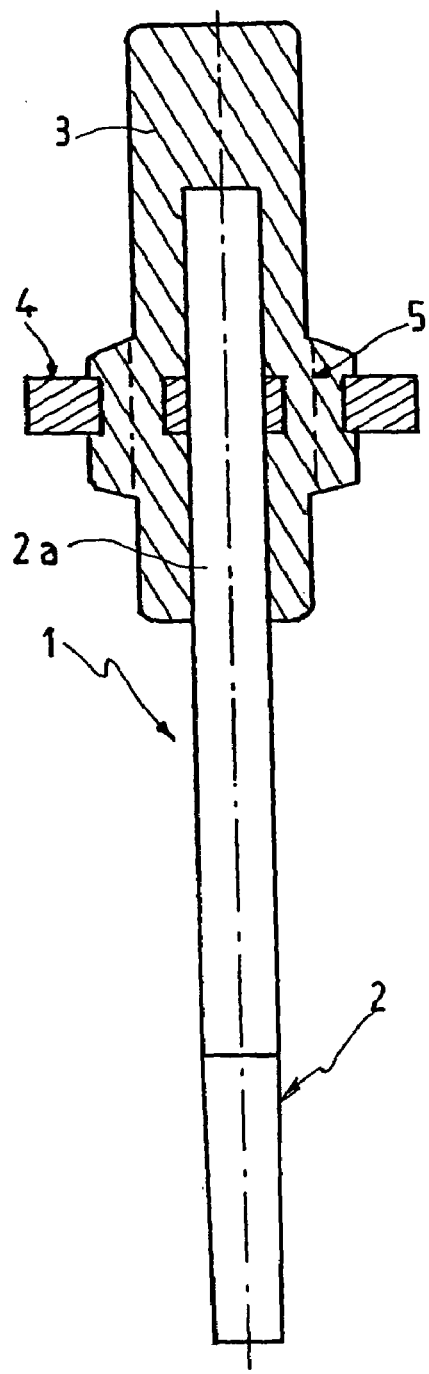
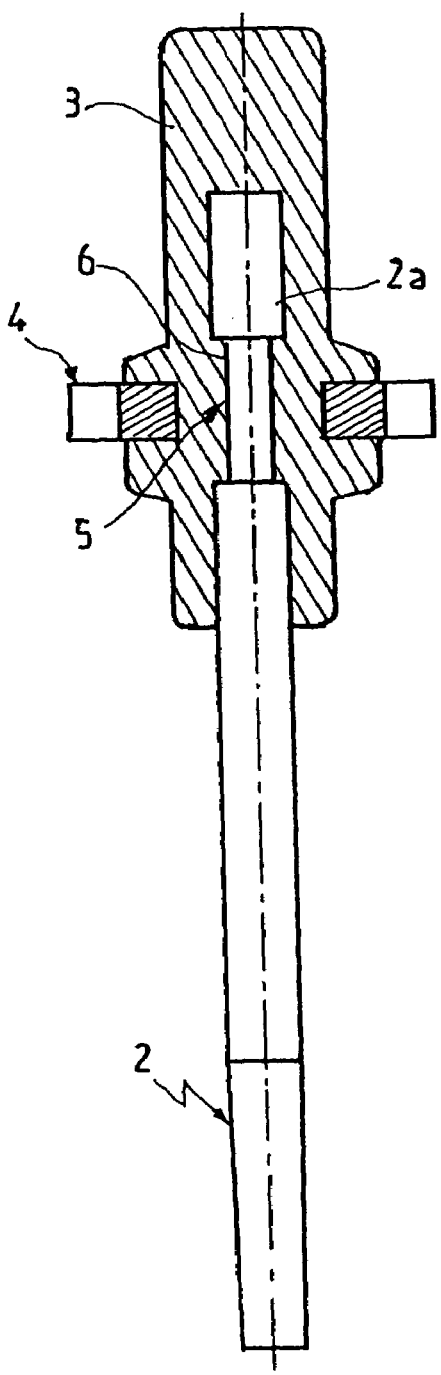
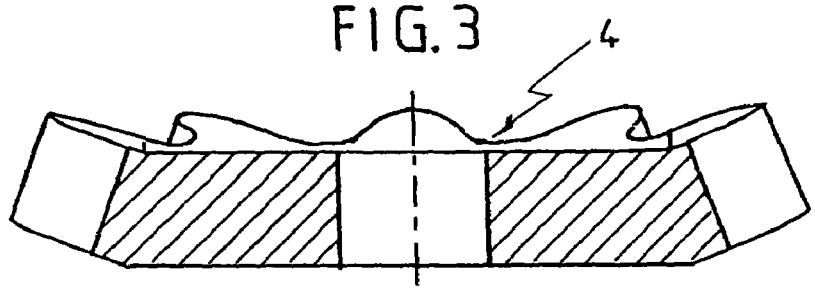

MECHANIZED DENTAL INSTRUMENT

BACKGROUND OF THE INVENTION

The present invention relates to a mechanized dental instrument, in particular, an endodontic instrument.

Generally, mechanized dental instruments include an active part, and a sleeve arranged at an end of the dental instrument which is remote from the active part. The sleeve of the dental instrument is provided with a rotary drive means which, when mounted in the head of a handpiece, is able to mesh directly with a rotary drive means located upstream of the head of the handpiece. An example of such structure is described, in particular, in commonly owned French Patent Application No. 2,759,574.

Such dental instruments are generally made partially of plastic overmolded on the active part. The major disadvantage of such a production method is the resistance of the teeth of the pinions which comprise the rotary drive means, at substantial torques, leading either to fracturing or premature wear of the teeth.

The object of the present invention is to provide a mechanized dental instrument which can remedy some or all of the aforementioned disadvantages.

SUMMARY OF THE INVENTION

To this end, and in accordance with the present invention, a mechanized dental instrument is provided which includes an active part, and a sleeve arranged at an end of the dental instrument which is remote from the active part. The sleeve of the dental instrument is provided with a rotary drive means which, when mounted in the head of a handpiece, is able to mesh directly with a rotary drive means located upstream of the head of the handpiece. The drive means is produced from a flat metal piece which is fixed to the active part by being slid over the axle of the active part. The metal piece is provided with at least one opening shaped in such a way as to permit circulation of the plastic material forming the sleeve during overmolding of the sleeve on the axle to ensure the connection of the rotary drive means on the axle.

In an alternative embodiment, the opening is formed by the combination of flats formed on the axle of the active part and the central orifice of the drive means, permitting introduction of the axle through the central orifice.

In an advantageous embodiment, the drive means is produced from a flat piece having toothing which is formed by cutting and then, if appropriate, by bending.

Further detail regarding the characteristics of the present invention will become apparent from a reading of the description of illustrative embodiments which is provided hereafter, with reference to the following drawings.

BRIEF DESCRIPTION OF THE DRAWINGS

FIG. 1 is a cross-sectional view of a mechanized dental instrument produced in accordance with the present invention.

FIG. 2 is a cross-sectional view similar to FIG. 1, showing an alternative embodiment of the mechanized dental instrument of the present invention.

FIG. 3 is a cross-sectional view of a pinion for the mechanized dental instrument.

DETAILED DESCRIPTION OF PREFERRED EMBODIMENTS

Figure 4:
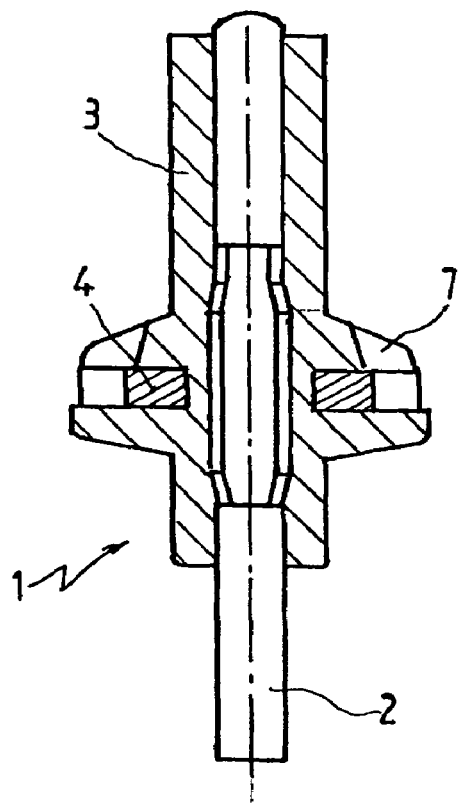
FIG. 4 is a cross-sectional view showing an alternative illustrative embodiment of the mechanized dental instrument of the present invention.

FIG. 1 shows a mechanized dental instrument 1 for use in endodontics. This instrument is conventionally made up of an active part 2, and a sleeve 3 arranged at an end of the instrument 1 which is remote from the active part 2. The end of the instrument which is remote from the active part 2 will be designated as an "axle" 2a in the remainder of the description which follows.

The sleeve 3 of the dental instrument 1 is provided with a pinion-type rotary drive means 4 which, when mounted in a head of a handpiece, meshes directly with a rotary drive means located upstream of the head of the handpiece.

In accordance with the present invention, the drive means 4 is produced from a flat metal piece which is fixed to the active part by being slid over the axle 2a. The piece is provided with at least one opening 5 which is shaped to permit circulation of the plastic material forming the sleeve 3 when the sleeve 3 is overmolded on the axle 2a. This ensures connection of the drive means 4 on the axle 2a. As can be seen from FIG. 1, the metal part 4 forming the drive means is provided with four uniformly distributed orifices 5, permitting circulation of the plastic material during overmolding of the sleeve 3 on the axle 2a of the active part 2.

In the alternative embodiment of the mechanized dental instrument which is shown in FIG. 2, the axle 2a of the active part 2 includes flats 6. After positioning of the metal piece, the flats 6 make it possible to overmold the formation of the sleeve in such a way that the plastic encompasses the flats 6, via the openings 5, in this way ensuring a connection in terms of rotation.

Referring to FIG. 3, the metal part 4 is advantageously produced from a flat piece, and the teeth forming the drive means are then cut. This reduces the cost of producing the metal part 4 when compared to a conventional solution. In addition, when necessary to ensure driven rotation by a conical gear, the toothing of the pinion is deformed so that the toothing is raised or lowered relative to the core of the pinion.

FIG. 4 shows another alternative embodiment of the mechanized dental instrument of the present invention. In this embodiment, the active part 2, namely the dental tool, extends all the way through the sleeve 3 of the dental instrument 1.

Figure 5:
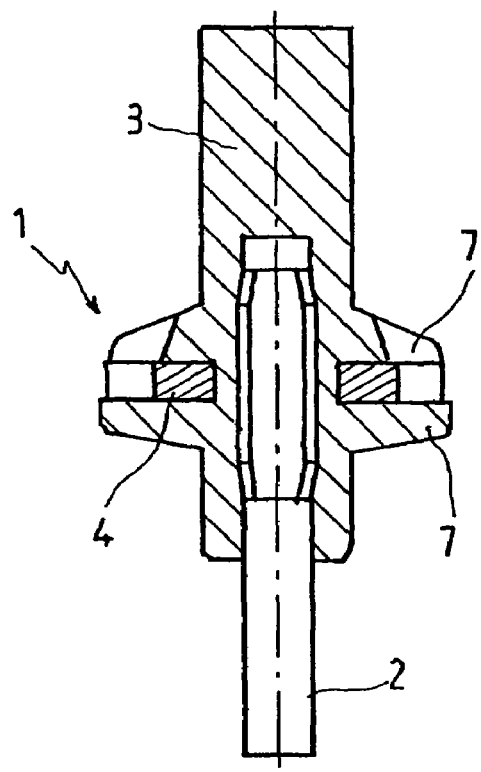
FIG. 5 is a cross-sectional view of a third alternative embodiment of the mechanized dental instrument of the present invention.
Figure 6:
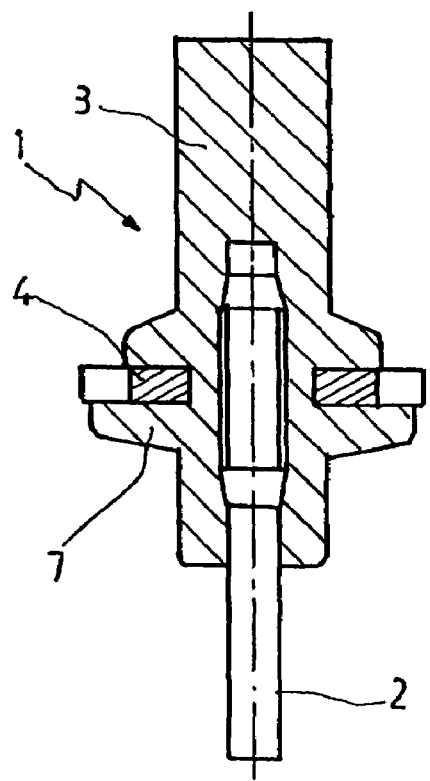
FIG. 6 is a cross-sectional view of a fourth alternative embodiment of the mechanized dental instrument of the present invention.

FIGS. 5 and 6 show alternative embodiments of the dental instrument having a protuberance 7 in the vicinity of the upper part of the sleeve 3. The protuberance 7 can enclose the metal piece 4 of the drive means on both sides, as is shown in FIG. 5, or only on the lower part of the metal piece 4, as is shown in FIG. 6. The protuberance 7 permits the capture of a force and/or a movement.

It will be appreciated from the above description that the dental instrument of the present invention is relatively simple to produce and permits greater resistance of the drive means. Although the invention has been described in connection with two particular embodiments, the present invention will further encompass all technical equivalents of the means described.

The invention claimed is:

1. A mechanized dental instrument comprising an active part, and a sleeve arranged at an end of the dental instrument which is remote from the active part,
   wherein the sleeve of the dental instrument is provided with a rotary drive which, when mounted in a head of a handpiece, is capable of directly meshing with a rotary drive located upstream of the head of the handpiece,
   wherein the active part includes an axle, and wherein the rotary drive is produced from a flat metal piece which is fixed to the active part by being slid over the axle of the active part, and
   wherein the piece is provided with at least one opening which is formed by a combination of flats formed on the axle of the active part and a central orifice associated with the rotary drive, and which is shaped to permit plastic material forming the sleeve to circulate in the opening during molding of the sleeve on the axle to ensure connection of the rotary drive on the axle.

2. The mechanized dental instrument of claim 1 wherein the piece forming the rotary drive has toothing cut into the piece.

3. The mechanized dental instrument of claim 2 wherein the toothing of the piece forming the rotary drive is bent relative to core portions of the piece.

4. The mechanized dental instrument of claim 1 wherein the active part extends through the sleeve, from one end of the sleeve to another end of the sleeve.

5. The mechanized dental instrument of claim 1 wherein the sleeve includes a protuberance for capturing a movement.

6. The mechanized dental instrument of claim 5 wherein the protuberance is associated with an upper part of the sleeve.

7. The mechanized dental instrument of claim 1 wherein the sleeve includes a protuberance for capturing a force.

8. The mechanized dental instrument of claim 7 wherein the protuberance is associated with an upper part of the sleeve.

9. The mechanized dental instrument of claim 1 wherein the sleeve includes a protuberance for capturing a movement and a force.

10. The mechanized dental instrument of claim 9 wherein the protuberance is associated with an upper part of the sleeve.

* * * * *